US006211194B1

(12) United States Patent
Westman et al.

(10) Patent No.: US 6,211,194 B1
(45) Date of Patent: Apr. 3, 2001

(54) SOLUTION CONTAINING NICOTINE

(75) Inventors: Eric C. Westman; Jed E. Rose, both of Durham; Keith F. Tomlin, Raleigh, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/070,263

(22) Filed: Apr. 30, 1998

(51) Int. Cl.$^7$ ................................................. A61K 31/44

(52) U.S. Cl. ..................... 514/300; 514/810; 514/813; 424/439; 424/455; 424/464; 424/489

(58) Field of Search ..................... 424/439, 455, 424/464, 489; 514/810, 813, 299, 300

(56) References Cited

U.S. PATENT DOCUMENTS

| | | | |
|---|---|---|---|
| 4,806,356 | 2/1989 | Shaw | 424/440 |
| 5,147,654 | * 9/1992 | Place et al. | 424/473 |
| 5,326,563 | * 7/1994 | Spindler et al. | 424/197.1 |
| 5,383,478 | 1/1995 | Rose et al. | 131/274 |
| 5,549,906 | 8/1996 | Santus | 424/440 |
| 5,594,030 | 1/1997 | Conte et al. | 514/553 |
| 5,747,512 | * 5/1998 | Keenan et al. | 514/343 |
| 5,810,018 | * 9/1998 | Monte | 131/270 |

FOREIGN PATENT DOCUMENTS

| | | |
|---|---|---|
| 899037 | 6/1984 | (FR) . |
| 2 142822A | 1/1985 | (GB) . |
| WO 88/03803 | 6/1988 | (WO) . |
| WO/91/09599 | 7/1991 | (WO) . |

OTHER PUBLICATIONS

Rose, "Nicotine Addiction and Treatment", vol. 47, *Annual Review Medical*, pp. 493–507 (1996).
Rose et al., "Subjective Response to Cigarette Smoking Following Airway Anaesthetization", vol. 9, *Additive Behaviors*, pp. 211–215 (1984).
Westman et al., "Airway Sensory Replacement with Nicotine Replacement for Smoking Cessation", vol. 107, *Chest*, pp. 1358–1364 (May, 1995).
Westman et al., "Nicotine as a Therapeutic Drug", vol. 56, No. 1, *North Carolina Medical Journal*, pp. 48–51, (Jan., 1995).
Report from the Centers for Disease Control and Prevention, "Cigarette Smoking among Adults—United States 1992, and Changes in Definition of Smoking", vol. 272, No. 1, pp. 14 and 16, *JAMA*, (1994).

Wald et al., "Prospective Study of Effect of Switching from Cigarette to Pipes or Cigars on Mortality from Three Smoking Related Diseases", vol. 314, *British Medical Journal*, pp. 1860–1863 (1997).

Schneider et al., "Efficacy of a Nicotine Inhaler in Smoking Cessation: a Double–blind, Placebo–Controlled Trial", vol. 91, No. 9, *Addiction*, pp. 1293–1306 (1996).

Benowitz et al., "Pharmacokinetics, Metabolism, and Pharmacodynamics of Nicotine", *Nicotine Psychopharmacology*, pp. 112–157, (1990).

Benowitz et al., "Stable Isotope Studies of Nicotine Kinetics and Bioavailability", vol. 49, No. 3, *Clinical Pharmacological Therapy*, pp. 270–277 (Mar., 1991).

Zins et al., "Pharmacokinetics of Nicotine Tartrate after Single–Dose Liquid Enema, Oral, and Intravenous Administration", vol. 37, *Clinical Pharmacology*, pp. 426–436, (1997).

Fiore et al., "The Effectiveness of the Nicotine Patch for Smoking Cessation", vol. 271, No. 24, *JAMA*, pp. 1940–1947 (Jun. 22/29, 1994).

Hoffmann et al., "The Changing Cigarette, 1950–1955", vol. 50, *Journal of Toxicology and Environmental Health*, pp. 307–364, (1997).

Sutherland et al., "Randomized Controlled Trial of Nasal Nicotine Spray in Smoking Cessation", vol. 340, *The Lancet*, pp. 324–329 (Aug. 8, 1992).

* cited by examiner

*Primary Examiner*—Dwayne C. Jones
*Assistant Examiner*—C. Delacroix-Muirheid
(74) *Attorney, Agent, or Firm*—Jenkins & Wilson, P.A.; Jennifer L. Skord

(57) ABSTRACT

A nicotine method and solution which utilizes an acidic solution containing nicotine. The solution is for use to treat various medical conditions, such as to reduce the need of a user of smoking tobacco to smoke tobacco, to reduce attention deficit disorder symptoms in a person who has attention deficit disorder, and/or to reduce Alzheimer's disease symptoms in a person who has Alzheimer's disease. The solution is palatable and may be introduced into the person by the person drinking it. Subsequent to drinking, the blood plasma levels are sufficient to reduce the need to smoke tobacco, to reduce attention deficit disorder symptoms, and/or to reduce Alzheimer's disease symptoms.

26 Claims, 2 Drawing Sheets

SOLUTION CONTAINING NICOTINE

TECHNICAL FIELD

The present invention relates in general to a smoking cessation aid, and more particularly to a nicotine containing solution useful as a smoking cessation aid to a user of smoking tobacco, and which is palatably acceptable to the user upon drinking by the user and which provides a sufficient amount of nicotine to the blood in order to reduce the need of the user to smoke tobacco. The nicotine solution is also useful in treating medical conditions other than addiction to the smoking of tobacco products, such as in treating attention deficit disorder and in treating Alzheimer's.

BACKGROUND OF THE INVENTION

Implicated in over one of every six deaths, cigarette smoking is the leading preventable cause of death in the United States. See, U.S.D.H.H.S., "The Health Benefits of Smoking Cessation", *A Report of the Surgeon General. Rockville. Md.: Public Health Service* (1990). Unfortunately, nearly 50 million Americans continue to smoke. See, "Cigarette Smoking Among Adults—United States", *Centers for Disease Control and Prevention*, (1992), and "Changes in Definition of Smoking", *JAMA*, Vol. 272, pp. 14–16 (1994). With currently available treatment, long-term smoking abstinence rates are generally less than 30%. See, Fiore, Smith, and Baker, "The Effectiveness of the Nicotine Patch in Smoking Cessation", *JAMA*, Vol. 271, pp. 1940–1947 (1994).

With the increasing recognition of the health hazards associated with the smoking of tobacco, particularly cigarette smoking, increasing attention has been focused on less harmful means to provide some of the satisfaction obtained by smoking. By temporarily giving the smoker an alternative source of nicotine, smoking withdrawal symptoms can be relieved and smoking abstinence facilitated. Some of the alternative sources rely on nicotine replacement through nicotine chewing gum, nicotine skin patches, nicotine nasal sprays, or nicotine vapor inhalers. See, Rose, J. E., "Nicotine Addiction and Treatment", *Ann. Rev. Med.*, Vol. 47, pp. 493–507 (1996). Also, buccal administration of a nicotine lozenge that has an alkaline pH is shown in U.S. Pat. No. 5,549,906 issued Aug. 27, 1996 to Santus.

In addition to smoking cessation, alternative forms of nicotine administration may have applicability in long-term maintenance, to reduce, if not entirely to eliminate, the harm resulting from smoking related diseases, which diseases, have been suggested by epidemiologic and basic biological research, to result from non-nicotine constituents in smoke. Not only does the "tar" fraction of tobacco smoke contains numerous potent carcinogens including nitrosamines and polynuclear aromatic hydrocarbons, but also other toxic fractions of tobacco smoke include carbon monoxide, hydrogen cyanide, and acrolein. See, Hoffman, D. and Hoffman, I., "The Changing Cigarette", *J. Toxicol. Environ. Health*, Vol. 50, pp. 307–364 (1997).

In contrast, little evidence exists to implicate nicotine in smoking related diseases. Epidemiologic evidence from studies of smokeless tobacco users and pipe and cigar smokers, who obtain substantial levels of nicotine but do not inhale significant quantities of smoke, show little increased morbidity and mortality, with the exception of cancer that probably results from non-nicotine tobacco constituents. See, Wald, N. J. and Waft, H. C., "Prospective Study of Effect of Switching from Cigarettes to Pipes or Cigars on Mortality from Three Smoking Related Diseases", *Br. Med. J.*, Vol. 314, pp. 1860–1863 (1997).

Aside from application in smoking cessation treatment, there is increasing evidence that nicotine may provide therapeutic benefits in the treatment of ulcerative colitis, and in neurodegenerative disorders such as Parkinson's disease and Alzheimer's disease. See, Westman, E. C., Levin, E. D., and Rose, J. E., "Nicotine as a Therapeutic Drug", *N.C. Med. J.*, Vol. 56, pp. 48–51 (1995), which shows intravenous administration of nicotine to treat ulcerative colitis. More studies vis-a-vis nicotine to treat ulcerative colitis are reported in Zins, Sandborn, Mays, Lawson, McKinney, Tremainc, Mahoney, Zinsmeister, Hurt, Offord, and Lipsky, "Pharmacokinetics of Nicotine Tartrate after Single-Dose Liquid Enema, Oral, and Intravenous Administration", *J.Clin. Pharmacol.*, Vol. 37, pp. 426–436 (May, 1997), which shows a nicotine solution (see, p. 428) that was drunk by the subjects to effect 45 $\mu$g of nicotine per kg of body weight, as well as a nicotine capsule that was swallowed by the subjects.

However, nicotine that is swallowed is absorbed from the small intestine and must pass through the liver prior to entering the general circulation. See, Benowitz, N. L., Porchet, H., and Jacob, P. I., "Pharmacokinetics, Metabolism, and Pharmacodynamics of Nicotine", Wonnacott, S., Russell, M. A. H., and Stolerman, I. P. (Eds.), *Nicotine Psychopharmacology* (pp. 112–157), Oxford: Oxford University Press (1990). Because the liver metabolizes much of the nicotine during this first pass absorption, it has generally been thought that nicotine swallowed by drinking a solution would not be an effective way to administer nicotine as an aid to smokers in their attempts to cease the smoking of tobacco since large doses of nicotine would have to be given to bypass the portal vein entry of the liver, and as is well known, nicotine has an aversive bitter, burning taste. This limits the acceptability of drinking a liquid solution of nicotine. The smokers would not drink nicotine because they would not like the taste of nicotine in a large enough amount when drunk in order to obviate the problem of the first pass absorption by the liver.

Moreover, although Jarvik, M. E., Glick, S. D., and Nakamura, R. K., "Inhibition of Cigarette Smoking by Orally Administered Nicotine", *Clin. Pharmacol. Ther.*, Vol. 11, pp. 574–576 (1970) showed that nicotine administered in capsules produced effects on smoking behavior presumably resulting from some nicotine absorption, and Benowitz, N. L., Jacob, P., Denaro, C., and Jenkins, R., "Stable Isotope Studies of Nicotine Kinetics and Bioavailability", *Clin. Pharmacol. Ther.*, Vol. 49, pp. 270–277 (1991) reported systemic levels similar to those produced by chewing nicotine gum after subjects swallowed capsules containing nicotine, it has nonetheless been felt that the large doses of nicotine needed to overcome first-pass liver metabolic effects would produce intolerable gastrointestinal irritation. Indeed, one of the subjects in the above-noted Benowitz et al. study entitled "Pharmacokinetics, Metabolism, and Pharmacodynamics of Nicotine" complained of nausea and abdominal cramping after a capsule containing nicotine was swallowed.

Thus, since each of the current nicotine replacement products, while having a role in smoking cessation and perhaps also in long-term maintenance, has significant drawbacks, there is a need for conveniently dispensed and well-tolerated nicotine formulations instead of cigarette smoking. For example, for many smokers nicotine chewing gum not only has an unappealing taste resulting from the local high concentration of nicotine in the mouth, but also is difficult to chew. See, Rose, J. E., "Nicotine Addiction and Treatment", *Ann. Rev. Med.*, Vol. 47, pp. 493–507 (1996). Nicotine patches do not provide rapid absorption of nicotine which some smokers prefer, can produce skin irritation in some individuals, and lack the desired sensory and ritual aspects of oral smoking behavior. See, Westman, E. C., Behm F. M., and Rose, J. E., "Airway Sensory Replacement as a Treatment for Smoking Cessation", Vol. 38, pp. 257–262 (1996). Nicotine nasal spray is often perceived as irritating, initially producing aversive reactions of sneezing and tearing. See, Sutherland, G., Stapleton, J. A., Russell, M. A. H., Jarvis, M. J., Hajek, P., Belcher, M., and Feyerabend, C., "Randomised Controlled Trial of Nasal Nicotine Spray in Smoking Cessation", *Lancet*, Vol. 340, pp. 324–329 (1992). Finally, the nicotine vapor inhaler can produce mouth and throat irritation, delivers low doses of nicotine often inadequate to satisfy many smokers, and some smokers view the puffing behavior as too similar to smoking tobacco as they are attempting to quit. See, Schneider, et al., "Efficacy of a Nicotine Inhaler in Smoking Cessation: A Double-Blind, Placebo-Controlled Trial", *Addiction*, Vol. 91, pp. 1293–1306 (1996). Thus, a continuing need exists for nicotine replacement products that are acceptable in terms of sensory aspects and yet provide an easily regulated nicotine dose that has an acceptable taste and can be self-administered.

SUMMARY AND OBJECTS OF THE INVENTION

In accordance with the present invention, disclosed is a method for providing nicotine to a human person by administration to the upper gastro-intestinal tract of a selected amount of nicotine. The method comprises providing a palatably acceptable solution containing a selected amount of nicotine, having an acidic pH, and being adapted for introduction into the person's upper gastro-intestinal tract, administering the solution to the person's upper gastro-intestinal tract so as to introduce the nicotine to the metabolism of the person, and periodically repeating the administration of the solution so as to administer a selected amount of the nicotine to the person's metabolism after pass through the portal vein entry of the liver so that the nicotine achieves a selected blood level of nicotine in the person in order to reduce the symptoms of the person. Preferably, the solution reduces symptoms of a medical condition in a person who has the medical condition by the nicotine amount being a therapeutically effective amount to achieve a sufficient blood level of the nicotine to reduce the symptoms. More preferably, the medical condition is selected from the group consisting of addiction to smoking tobaccco, attention deficit disorder, Alzheimer's disease, Parkinson's disease, inability to regulate body weight at a level proper for body height, depression, ulcerative colitis, and combinations thereof.

In one embodiment, provided is a method for reducing tobacco smoking in a human user by administration to the upper gastrointestinal tract of a therapeutically effective amount of nicotine. The method comprises providing a palatably acceptable solution containing a therapeutically effective amount of nicotine, having an acidic pH, and being adapted for introduction into the human's upper gastrointestinal tract. The solution is administered to the human's upper gastrointestinal tract to introduce the nicotine to the human's metabolism, and periodically the administration is repeated, to administer a therapeutically effective amount of the nicotine to the human's metabolism after pass through the portal vein entry of the liver so that the nicotine achieves a sufficient blood level of nicotine in the human to reduce the human's need to smoke tobacco. In another embodiment, the method may be for administering a nicotine solution, as described in the paragraph above, to a human having attention deficit disorder or Alzheimer's disease to reduce the human's respective attention deficit disorder symptoms or Alzheimer's disease symptoms.

Thus, one object of the present invention is that although the general belief was that nicotine liquid would prove unacceptable for drinking due to the acrid, burning, bitter taste of nicotine in aqueous solution, nicotine indeed can be delivered effectively in an appropriate concentration in solution in a form that is palatable, and which produces significant systemic levels of nicotine as measured in venous blood, after pass through the liver.

An advantage of the present invention is to provide an acceptable level of nicotine-related sensory stimulation in the throat that may be important in reducing craving for cigarettes, such as the craving reported by Rose et al., "Subjective Response to Cigarette Smoking Following Airway Anesthetization", *Addict. Behav.*, Vol. 9, pp. 211–215 (1984). A further advantage of the present invention is that by ensuring liquid intake along with nicotine, the local concentration of nicotine in the upper gastrointestinal tract can also be regulated to lessen the likelihood of cramping due to high local concentrations of nicotine, such as from swallowing a capsule.

Some of the objects and advantages of the invention having been stated above, others will become evident as the description proceeds, when taken in connection with the accompanying drawing and Laboratory Examples as best described below.

DETAILED DESCRIPTION OF THE INVENTION

Figure 1:
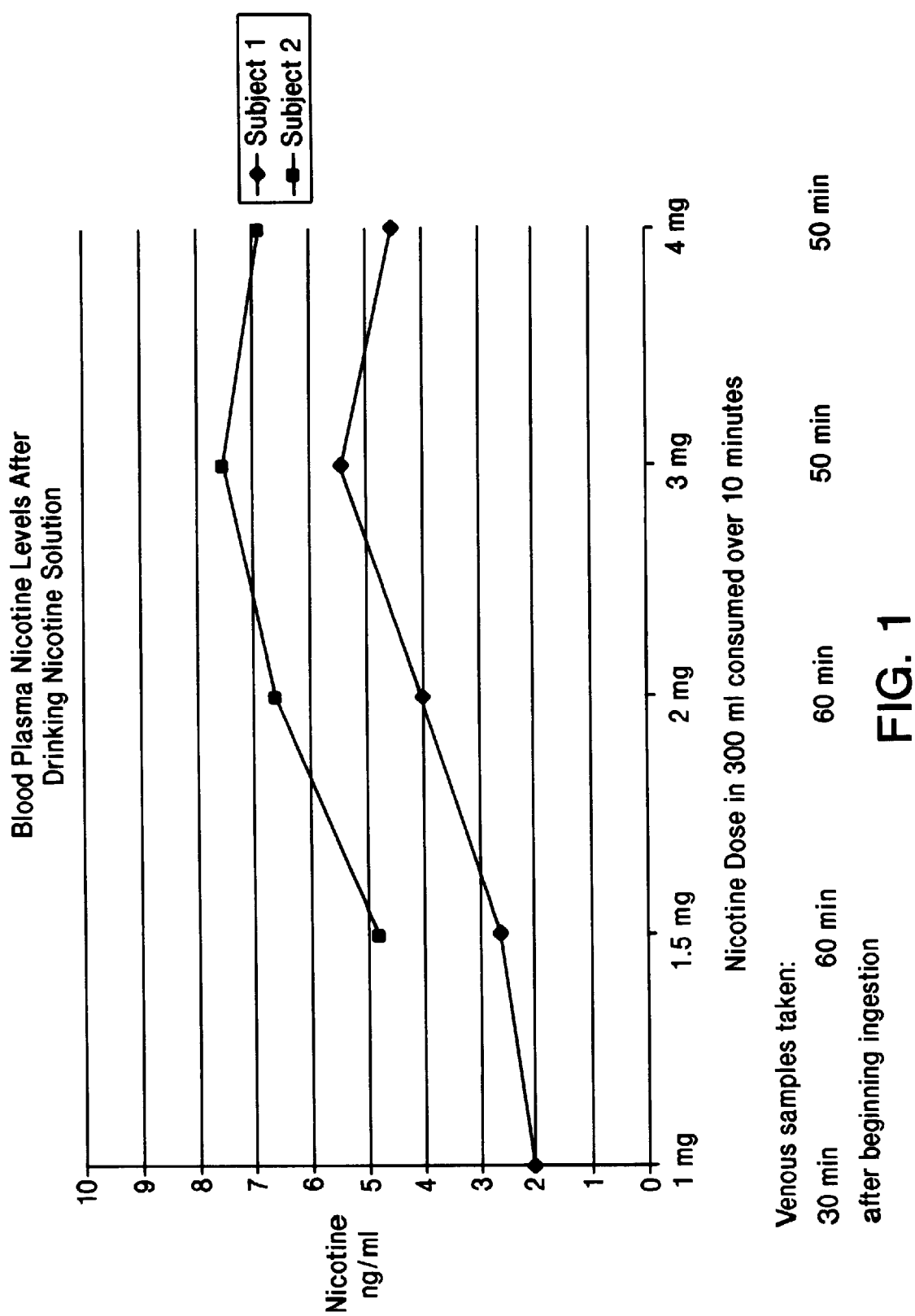
FIG. 1 is a graph showing blood plasma levels after 2 subjects drank various nicotine solutions in accordance with the invention.

The present invention provides a new and surprisingly effective method and product for delivering a nicotine containing solution to treat various medical conditions, such as to give relief of the craving for tobacco smoking (for instance, the smoking of cigarettes), to treat and alleviate symptoms of attention deficit disorder, and/or to treat and alleviate the symptoms of Alzheimer's disease. More particularly, nicotine is placed in a solution, for instance an aqueous solution. In addition to employing water as the solvent for the nicotine to be in solution, other solvents may be employed as long as they are acceptable for human ingestion and dissolve the nicotine. For example, ethyl alcohol (i.e., beer, wine, or whiskey) and/or milk may be employed as the solvent. Hence, a nicotine liquid is provided for administration to the upper gastrointestinal tract of a person, for instance, for the user of smoking tobacco to drink. In addition to administration by a person swallowing a drink by way of the mouth, contemplated also is administration to the esophagus, stomach, and/or duodenum, such as by way of a feeding tube. Administration of nicotine in accordance with the present invention is specifically intended to exclude administration by swallowing tablets and/or capsules, by buccal, and by sublingual.

The amount of nicotine in the total amount of solution for a dose should be at least about 0.5 mg of the nicotine per about 300 ml of the nicotine solution. Preferably, the amount of the nicotine ranges from about 1 to about 42 mg of nicotine per 300 ml of nicotine solution, more preferably ranges from about 1 to about 36 mg of nicotine per 300 ml of nicotine solution, even more preferably ranges from about 2 to about 26 mg of nicotine per 300 ml of nicotine solution, and most preferably is about 4 to about 12 mg of nicotine per 300 ml of nicotine solution.

The nicotine employed may be levo nicotine, dextro nicotine, or a racemic mixture of both levo nicotine and dextro nicotine. As is well known, the (−)isomer is naturally occurring nicotine, and is a weak base with a pKa of 8.0 in aqueous solution at 25° C. The tobacco plant has this (−)isomer. As is also well known, the burning of tobacco in a product such a cigarette changes some of the (−)nicotine into a racemic mixture of (±)isomers of nicotine. Thus, a person who is smoking is also inhaling some of the (+)isomer of nicotine, which does not naturally occur. As noted in the above-mentioned two articles by Benowitz et al., the human body metabolizes (−), (+), or (±) mixtures at essentially the same rate.

As discussed in detail above, nicotine, when taken orally, has a very bitter, aversive taste. To make the nicotine solution of the present invention be palatable, particularly when the solution is a drink to be swallowed by way of the mouth so that the solution will touch the taste buds in the mouth, the pH must be adjusted to be acidic. More specifically, the pH should be adjusted to be less than about 6.9, and more preferably less than about 5.5, and most preferably in a range from about 2.0 to about 4.0. Various acids may be employed as pH control agents for the pH adjustment, and such acids include, but are not limited to, carbonic acid, citric acid, acetic acid, tartaric acid, maleic acid, ascorbic acid, adipic acid, and combinations thereof. Food acids are very suitable.

Due to the pH control of the nicotine solution to be acidic, the nicotine solution is made containing a relatively large amount of nicotine, as compared to previous attempts at nicotine solutions to be drunk through the mouth by the subject. The desired amount of nicotine in the inventive nicotine solution is noted above, but regardless, the amount is sufficient to obviate the problem of the first-pass absorption to the liver, so that a therapeutically effective amount of the nicotine is administered to the user's metabolism after pass through the portal vein entry of the liver so that the nicotine achieves a sufficient blood level in the user in order to reduce the need of a tobacco smoker for tobacco smoke, to treat and alleviate the symptoms of attention deficit disorder in a person who has the disorder, and/or to treat and alleviate the symptoms of Alzheimer's disease in a person who has the disease.

Dosing should be repeated with at least 1 dose, such as a drink, of the nicotine solution per day, and preferably 1 dose, such as a drink, every 1 to 2 hours during the waking hours of the person being dosed with the nicotine solution in order to maintain a sufficient blood level of nicotine in order to reduce the need of the person to smoke tobacco, reduce the person's attention deficit disorder symptoms, and/or reduce the person's Alzheimer's disease symptoms. Preferably, the incidence of dosing and the amount of nicotine in the nicotine solution is adjusted for the individual person so that the blood level of the nicotine does not rise above about 35 ng of nicotine per 1 ml of blood, but of course, this will vary depending on the extent of the particular person's addiction to the smoking of tobacco, attention deficit disorder symptoms, and/or Alzheimer's disease symptoms.

Figure 2:
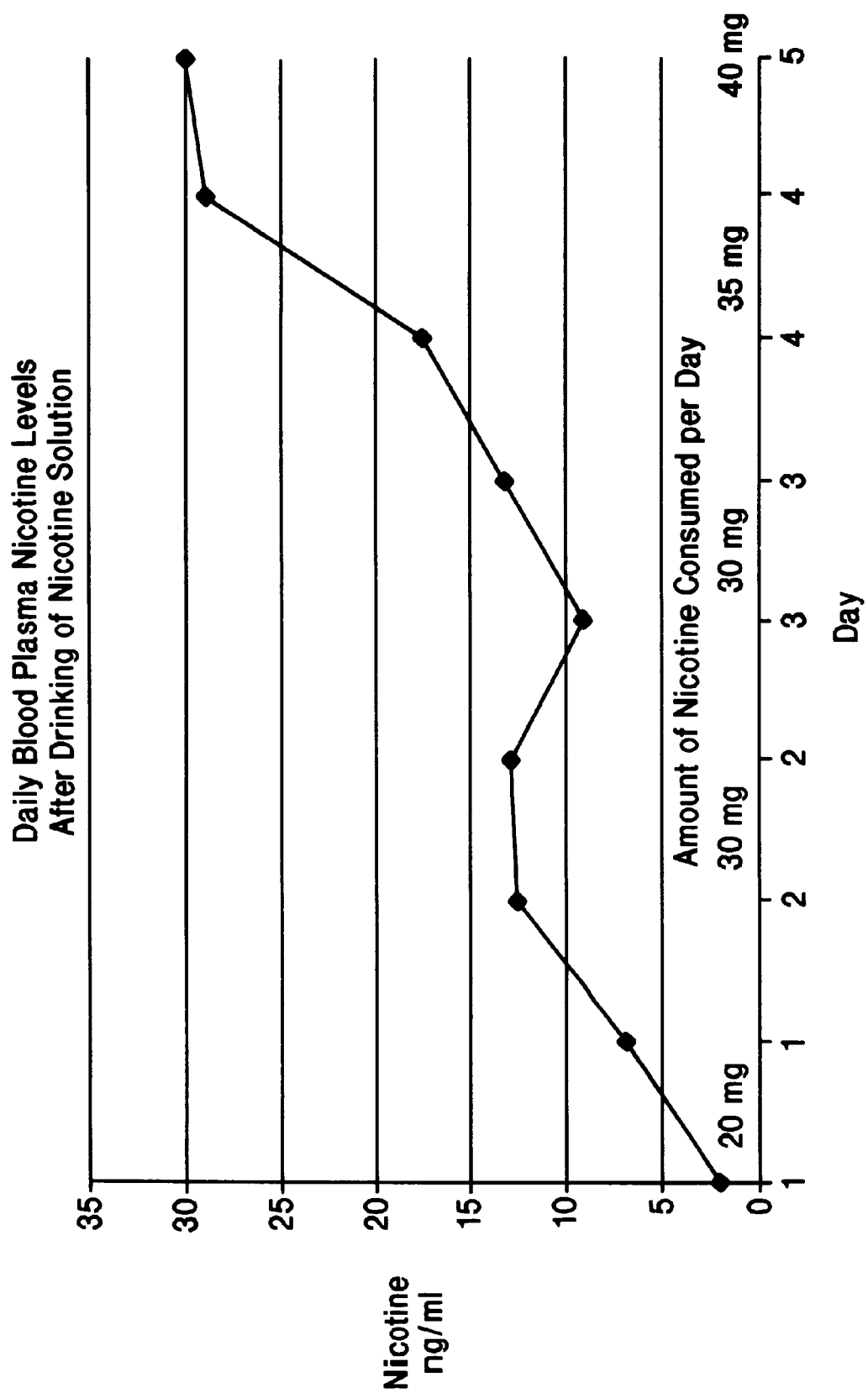
FIG. 2 is a graph showing blood plasma levels after a subject drank various nicotine solutions in accordance with the invention.

Desirably, within about 30 to about 80 minutes, more preferably, within about 50 minutes, of the nicotine solution being administered (such as by drinking), the blood plasma nicotine level of the person should be at least about 1.5 ng of nicotine per about 1 ml of blood. Blood plasma levels of about 2 to about 7.5 ng per ml of blood are typical for 1 dose of about 1 to 4 mg per day of nicotine, as can be seen in FIG. 1, and about 2.5 to 30 ng for multiple daily dosing to achieve a total intake per day of about 20 to 40 mg, as can be seen in FIG. 2.

In order to enhance further the palatability of the nicotine solution, for instance, for when the solution is to be swallowed through the mouth by drinking, optionally included in the nicotine solution may be a flavoring. The amount of optional flavoring is not critical, and typically can be adjusted according to the personal preference of the person who will drink the nicotine containing solution. Suitable flavorings include, but are not limited to, sugar, coffee, beer, wine, whiskey, fruit juice, milk, soda, and the like. Suitable kinds of fruit juice are cranberry juice, grapefruit juice, lime juice, and orange juice. Suitable kinds of milk are whole, 2%, 1%, and chocolate. Suitable kinds of soda are spring water, seltzer water, tonic water, root beer, cola, ginger ale, Sprite® and Dr. Pepper®. Besides further enhancing the palatability of the nicotine solution, flavorings such as coffee, milk, and/or fruit juice may also contribute to maintaining the pH of the nicotine solution in the acidic range.

In addition to the nicotine solution discussed above, which solution may be conveniently marketed as a bottled and/or canned beverage, the invention contemplates in another embodiment a packet of nicotine powder, with an appropriate amount of pH control agent, so that the user could open the packet and pour the powder into the user's desired beverage, such as a glass of water.

LABORATORY EXAMPLES

Example 1

Part A. To test the efficacy of the instant invention, applicants conducted a controlled laboratory study in which 2 subject non-smokers drank various nicotine solutions. Each sample was prepared by adding the respective amount of levo nicotine (purchased from Kodak), as indicated in the graph in FIG. 1, to an aqueous cola beverage (Diet Coke®) to make each sample be a total of 300 ml of solution.

Each subject drank 1 drink per day, with each drink being drunk over a time span of 10 minutes. Specifically, on day 1, each subject drank 1 drink containing 1 mg of nicotine; on day 2, each subject drank 1 drink containing 1.5 mg of nicotine; on day 3, each subject drank 1 drink containing 2 mg of nicotine; on day 4, each subject drank 1 drink containing 3 mg of nicotine; and on day 5, each subject drank 1 drink containing 4 mg of nicotine.

All nicotine solutions had a pH of 3.2 that was due to the carbonic acid already present in the cola beverage. The blood plasma levels of the 2 subjects were tested for nicotine content after each drink at the times indicated below the graph in FIG. 1, and were found to range from about 2 to about 7 ng of nicotine per ml of blood as plotted in the graph of FIG. 1.

Part B. Additionally, as summarized in the Table below, each subject drank the following drinks (1 drink each day), each drink being 15 ml of a solution containing 10 mg of nicotine per 300 ml total solution.

TABLE

| Day | Scratch | pH | Beverage |
| --- | --- | --- | --- |
| 1 | 1.000 | 2.200 | Spring Water + Citric |
| 2 | 1.000 | 2.300 | Lime Juice Conc. |
| 3 | 1.000 | 2.600 | Cranberry Juice |
| 4 | 1.500 | 2.600 | Spring Water + Citric |
| 5 | 2.500 | 2.600 | Tonic Water |
| 6 | 1.500 | 2.900 | Dr. Pepper |
| 7 | 2.000 | 2.900 | Ginger Ale |
| 8 | 3.000 | 2.900 | Spring Water + Citric |
| 9 | 3.500 | 3.000 | Spring Water + Citric |
| 10 | 2.000 | 3.300 | Sprite |
| 11 | 2.500 | 3.300 | Grapefruit Juice |
| 12 | 1.000 | 3.500 | Merlot Wine |
| 13 | 1.500 | 3.500 | Chardonnay Wine |
| 14 | 1.500 | 3.800 | Orange Juice |
| 15 | 1.500 | 4.100 | Heineken Beer |
| 16 | 2.500 | 4.100 | Seltzer Water |
| 17 | 2.000 | 4.200 | Canadian Mist Whiskey |
| 18 | 3.000 | 4.200 | Budweiser Beer |
| 19 | 2.500 | 4.300 | Pete's Wicked Ale Beer |
| 20 | 5.000 | 4.500 | Diet Root Beer |
| 21 | 5.000 | 4.900 | Coffee |
| 22 | 2.000 | 6.200 | Spring Water |
| 23 | 3.500 | 6.200 | Spring Water |
| 24 | 4.000 | 6.500 | 2% Milk |
| 25 | 4.000 | 6.600 | Chocolate Milk |

Indicated in the second column of the Table is the average of the 2 subjects' ratings calculated from each subject's respective throat scratch on a scale of 1 (no scratch) to 7 (extreme scratch). This data demonstrates that the second best throat sensory effect came from the solutions of nicotine in milk (both the 2% milk and the chocolate milk), and the best came from the solutions of nicotine in diet root beer and in coffee.

Part C. To test the efficacy of the instant invention further, applicants conducted another controlled laboratory study in which a subject non-smoker drank various nicotine solutions over 5 consecutive days. Each sample was prepared by adding the 5 mg of levo nicotine (purchased from Kodak) to an aqueous cola beverage (Diet Coke®) to make each sample be a total of 300 ml of solution.

The subject drank several drinks per day, with each drink being drunk over a time span of 10 minutes to 30 minutes, each drink at a different time throughout the subject's waking hours, to achieve the total daily intake of nicotine as indicated in the graph in FIG. 2. Specifically, on day 1, the subject drank 4 drinks to achieve a total intake for the day of 20 mg of nicotine; on day 2, the subject drank 6 drinks to achieve a total intake for the day of 30 mg of nicotine; on day 3, the subject drank 6 drinks to achieve a total intake for the day of 30 mg of nicotine; on day 4, the subject drank 7 drinks to achieve a total intake for the day of 35 mg of nicotine; and on day 5, the subject drank 8 drinks to achieve a total intake for the day of 40 mg of nicotine.

All nicotine solutions had a pH of 3.2 that was due to the carbonic acid already present in the cola beverage. The blood plasma levels of the subject were tested for nicotine content twice each day at 12:30 p.m. and at 6:00 p.m., except only once on day 5, and were found to range from about 2.5 to about 30 ng of nicotine per ml of blood as plotted in the graph of FIG. 2.

Example 2

Repeated may be Example 1, except with 2 smokers. Smoking will not be permitted during the study, and the subjects will arrive at the laboratory after 24 hours abstinence from smoking (confirmation by expired air carbon monoxide analysis).

Subsequent to the test, the subjects will be asked to rate their craving for cigarettes and other smoking withdrawal symptoms experienced after the drinking of the nicotine solutions. Both subjects should report the craving for cigarettes, as well as withdrawal symptoms, are tending to decrease.

Also subsequent to each drink, the blood plasma levels of the 2 subjects will be tested for nicotine content, and should be similar to those reported in Example 1.

Example 3

Repeated may be Example 1, except with 2 persons who have attention deficit disorder. Smoking will not be permitted during the study, and if the subjects are smokers, they will arrive at the laboratory after 24 hours abstinence from smoking (confirmation by expired air carbon monoxide analysis), to ensure nicotine effects are due to the nicotine in the solutions and not to nicotine in smoking tobacco products.

Subsequent to the test, the subjects will be asked to rate their attention deficit disorder symptoms experienced after the drinking of the nicotine solutions. Both subjects should report the symptoms are tending to decrease.

Also subsequent to each drink, the blood plasma levels of the 2 subjects will be tested for nicotine content, and should be similar to those reported in Example 1.

Example 4

Repeated may be Example 1, except with 2 persons who have Alzheimer's disease. Smoking will not be permitted during the study, and if the subjects are smokers, they will arrive at the laboratory after 24 hours abstinence from smoking (confirmation by expired air carbon monoxide analysis), to ensure nicotine effects are due to the nicotine in the solutions, and not to the nicotine in smoking tobacco products.

Subsequent to the test, the subjects will be asked to rate their Alzheimer's disease symptoms experienced after drinking of the nicotine solutions. Both subjects should report the symptoms are tending to decrease.

Also subsequent to each drink, the blood plasma levels of the 2 subjects will be tested for nicotine content, and should be similar to those reported in Example 1.

These results support applicants' belief that nicotine solutions described herein may be useful in alleviating the desire to smoke and thereby facilitating smoking cessation.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for providing nicotine to a person by administration to the upper gastro-intestinal tract of a selected amount of nicotine, said method comprising:

(a) providing a palatably acceptable solution containing a therapeutically effective amount of nicotine, having an acidic pH, and being adapted for introduction into the person's upper gastrointestinal tract, and including a flavoring in the nicotine solution wherein the flavoring is selected from the group consisting of sugar, coffee, beer, wine, whiskey, fruit juice, milk, soda, and combinations thereof;

(b) administering the nicotine solution to the person's upper gastro-intestinal tract so as to introduce the nicotine to the metabolism of the person, wherein the administering is free of buccal administering and free of sublingual administering; and (c) periodically repeating (b), so as to administer a selected amount of the nicotine to the person's metabolism after the first-pass absorption to the liver so that the nicotine achieves a selected blood level in the person.

2. A method for reducing the incidence of tobacco smoking in a human user by administration to the upper gastro-intestinal tract of a therapeutically effective amount of nicotine, said method comprising:

(a) providing a palatably acceptable solution containing a therapeutically effective amount of nicotine, having an acidic pH, and being adapted for introduction into the user's upper gastro-intestinal tract, and including a flavoring in the nicotine solution wherein the flavoring is selected from the group consisting of sugar, coffee, beer, wine, whiskey, fruit juice, milk, soda, and combinations thereof;

(b) administering the nicotine solution to the user so as to introduce the nicotine to the metabolism of the user, wherein the administering is free of buccal administering and free of sublingual administering; and (c) periodically repeating (b), so as to administer a therapeutically effective amount of the nicotine to the user's metabolism after the first-pass absorption to the liver so that the nicotine achieves a sufficient blood level in the user in order to reduce the need of the user to smoke tobacco.

3. A method for providing nicotine to a person by administration to the upper gastro-intestinal tract of a selected amount of nicotine, said method comprising:

(a) providing a palatably acceptable solution containing a therapeutically effective amount of nicotine, having a pH less than about 5.5, and being adapted for introduction into the person's upper gastro-intestinal tract;

(b) administering the nicotine solution to the person's upper gastro-intestinal tract so as to introduce the nicotine to the metabolism of the person; and (c) periodically repeating (b), so as to administer a selected amount of the nicotine to the person's metabolism after the first-pass absorption to the liver so that the nicotine achieves a selected blood level in the person.

4. The method according to claim 3, wherein the nicotine solution has a pH from about 2.0 to about 4.0.

5. The method according to claim 3, wherein the amount of the nicotine contained in the nicotine solution is at least about 0.5 milligram of the nicotine per about 300 milliliters of the nicotine solution.

6. The method according to claim 5, wherein the nicotine solution contains from about 1 milligram to about 42 milligrams of the nicotine per about 300 milliliters of the nicotine solution.

7. The method according to claim 3, wherein the blood level of the nicotine is at least about 1.5 nanograms of the nicotine per 1 milliliter of the blood.

8. The method according to claim 7, wherein the blood level of the nicotine is from about 2 nanograms to about 35 nanograms of the nicotine per about 1 milliliter of blood.

9. The method according to claim 3, wherein the nicotine is selected from the group consisting of levo nicotine, dextro nicotine, and racemic mixtures of the foregoing.

10. The method according to claim 3, further including a flavoring in the nicotine solution.

11. The method according to claim 10, wherein the flavoring is selected from the group consisting of sugar, coffee, beer, wine, whiskey, fruit juice, milk, soda, and combinations thereof.

12. The method according to claim 3, wherein the administration to the upper gastro-intestinal tract is by way of a portion of the upper gastro-intestinal tract selected from the group consisting of a mouth, an esophagus, a stomach, a duodenum, and a combination thereof.

13. The method of claim 3, wherein providing the nicotine solution reduces symptoms of a medical condition in a person who has the medical condition by the nicotine amount being a therapeutically effective amount to achieve a sufficient blood level of the nicotine to reduce the symptoms.

14. The method of claim 13, wherein the medical condition is selected from the group consisting of addiction to smoking tobacco, attention deficit disorder, Alzheimer's disease, Parkinson's disease, inability to regulate body weight at a level proper for body height, depression, ulcerative colitis, and combinations thereof.

15. A method for providing nicotine to a person by swallowing a selected amount of nicotine, said method comprising:

(a) providing a palatably acceptable aqueous solution containing about 0.5 to about 42 milligrams of nicotine per about 300 milliliters of nicotine solution and having a pH less than about 5.5;

(b) drinking the solution so as to introduce the nicotine to the metabolism of the person; and (c) periodically repeating (b) at least 1 time per day, so as to achieve a blood level of at least 1.5 nanograms of the nicotine per about 1 milliliter of blood in the person within about 30 to about 80 minutes of each repeating of (b).

16. A method for reducing the incidence of tobacco smoking in a human user by administration to the upper gastro-intestinal tract of a therapeutically effective amount of nicotine, said method comprising:

(a) providing a palatably acceptable solution containing a therapeutically effective amount of nicotine, having a pH less than about 5.5, and being adapted for introduction into the user's upper gastro-intestinal tract;

(b) administering the nicotine solution to the user so as to introduce the nicotine to the metabolism of the user; and (c) periodically repeating (b), so as to administer a therapeutically effective amount of the nicotine to the user's metabolism after the first-pass absorption to the liver so that the nicotine achieves a sufficient blood level in the user in order to reduce the need of the user to smoke tobacco.

17. The method according to claim 16, wherein the nicotine solution has a pH from about 2.0 to about 4.0.

18. The method according to claim 16, wherein the therapeutically effective amount of the nicotine contained in the nicotine solution is at least about 0.5 milligram of the nicotine per about 300 milliliters of the nicotine solution.

19. The method according to claim 18, wherein the nicotine solution contains from about 1 milligram to about 42 milligrams of the nicotine per about 300 milliliters of the nicotine solution.

20. The method according to claim 16, wherein the blood level of the nicotine is at least about 1.5 nanograms of the nicotine per 1 milliliter of the blood.

21. The method according to claim 20, wherein the blood level of the nicotine is from about 2 nanograms to about 35 nanograms of the nicotine per about 1 milliliter of the blood.

22. The method according to claim 16, wherein the nicotine is selected from the group consisting of levo nicotine, dextro nicotine, and racemic mixtures of the foregoing.

23. The method according to claim 16, further including a flavoring in the nicotine solution.

24. The method according to claim 23, wherein the flavoring is selected from the group consisting of sugar, coffee, beer, wine, whiskey, fruit juice, milk, soda, and combinations thereof.

25. The method according to claim 16, wherein the administration to the upper gastro-intestinal tract is by way of a portion of the upper gastro-intestinal tract selected from the group consisting of a mouth, an esophagus, a stomach, a duodenum, and a combination thereof.

26. A method for reducing the incidence of tobacco smoking in a human user by swallowing a therapeutically effective amount of nicotine, said method comprising:
  (a) providing a palatably acceptable aqueous solution containing about 0.5 to about 42 milligrams of nicotine per about 300 milliliters of nicotine solution and having a pH less than about 5.5;
  (b) drinking the solution so as to introduce the nicotine to the metabolism of the user; and
  (c) periodically repeating (b) at least 1 time per day, so as to achieve a blood level of at least about 1.5 nanograms of the nicotine per about 1 milliliter of blood in the user within about 30 to about 80 minutes of each repeating of (b).

* * * * *

UNITED STATES PATENT AND TRADEMARK OFFICE
CERTIFICATE OF CORRECTION

PATENT NO. : 6,211,194 B1  Page 1 of 1
DATED : April 3, 2001
INVENTOR(S) : Eric C. Westman et al.

It is certified that error appears in the above-identified patent and that said Letters Patent is hereby corrected as shown below:

<u>Column 1,</u>
Line 2, please add the following:
　　　　　　-- Grant Statement

The Veterans Administration of the United States provided funding for this invention. Therefore, the United States Government has certain rights in the invention. --

Signed and Sealed this

Fifth Day of March, 2002

Attest:

JAMES E. ROGAN
*Attesting Officer*　　*Director of the United States Patent and Trademark Office*